(12) United States Patent
Koopmans

(10) Patent No.: US 6,466,022 B1
(45) Date of Patent: Oct. 15, 2002

(54) METHOD FOR MEASURING THE PROPORTION OF PARTICLES IN THE EXHAUST GASES FROM AN INTERNAL COMBUSTION ENGINE

(75) Inventor: Lucien Koopmans, Gothenburg (SE)

(73) Assignee: Volvo Car Corporation, Gothenburg (SE)

( * ) Notice: Subject to any disclaimer, the term of this patent is extended or adjusted under 35 U.S.C. 154(b) by 0 days.

(21) Appl. No.: 09/555,481
(22) PCT Filed: Nov. 30, 1998
(86) PCT No.: PCT/SE98/02180
  § 371 (c)(1),
  (2), (4) Date: Oct. 2, 2000
(87) PCT Pub. No.: WO99/31369
  PCT Pub. Date: Jun. 24, 1999

(30) Foreign Application Priority Data

Dec. 1, 1997 (SE) .............................................. 9704460

(51) Int. Cl.$^7$ ................................................. F02P 17/00
(52) U.S. Cl. ..................................................... 324/399
(58) Field of Search ................................ 324/393, 397, 324/399, 402, 404; 123/305, 435, 703; 60/274, 276, 297

(56) References Cited

U.S. PATENT DOCUMENTS

| | | | |
|---|---|---|---|
| 4,307,061 A | | 12/1981 | Sarholz |
| 4,862,093 A | * | 8/1989 | Jiewertz .................... 324/464 |
| 5,180,983 A | | 1/1993 | Murata et al. |
| 5,237,280 A | | 8/1993 | Arnold et al. |

FOREIGN PATENT DOCUMENTS

EP  0 627 622  12/1994

\* cited by examiner

*Primary Examiner*—N. Le
*Assistant Examiner*—Etienne LeRoux
(74) *Attorney, Agent, or Firm*—Young & Thompson

(57) ABSTRACT

A method of measuring the particle content, in particular the soot particle content, in the exhaust gases of an internal combustion engine using a sensor arranged in contact with the exhaust gases. The sensor detects in at least one combustion chamber of the internal combustion engine an electrical quantity, the size of which is dependent on the particle content in the exhaust gases. The level of a measurement signal output from the sensor, the signal is dependent on the detected quantity, is determined and compared with a desired value level of a signal which corresponds to a desired particle content in the exhaust gases.

20 Claims, 2 Drawing Sheets

METHOD FOR MEASURING THE PROPORTION OF PARTICLES IN THE EXHAUST GASES FROM AN INTERNAL COMBUSTION ENGINE

BACKGROUND OF THE INVENTION

The present invention relates to a method of measuring the particle content, in particular the soot particle content, in the exhaust gases of an internal combustion engine by means of a sensor arranged in contact with the exhaust gases.

In piston engines, in which the fuel is injected directly into the combustion chamber, such as GDI (Gasoline Direct Injection) engines and diesel engines, problems of soot formation in the exhaust gases occur under certain operating conditions. This is due inter alia to the fact that the air/fuel mixture in the combustion chamber is what is referred to as layered or, more usually, stratified. A further reason for soot formation in the exhaust gases is that, under certain operating conditions, the fuel injected directly into the cylinder strikes the piston and the surrounding cylinder walls. In GDI engines, it is desirable under certain operating conditions to work with a stratified air/fuel mixture because a lower fuel consumption can then be obtained. In order to ignite a lean air fuel/mixture in the combustion chamber using a spark plug, a locally richer mixture must be produced around the region where the spark plug is located. This state with the mixture being divided into a lean and a rich mixture in the combustion chamber is consequently referred to as stratified. The opposite of a stratified air/fuel mixture is a homogeneous air/fuel mixture.

When soot is formed in the exhaust gases, the combustion of the fuel injected into the combustion chamber becomes incomplete, which means that substances that have an effect on the environment are formed in the exhaust gases. In order to prevent soot formation in the exhaust gases, various measures can be taken. For example, the moment of fuel injection can be regulated and/or the moment of ignition of the air/fuel mixture in the combustion chamber can be regulated. It is also possible to regulate the ratio of air to fuel in the air/fuel mixture. However, the problem is detecting when soot formation in the exhaust gases is taking place and how much soot is being formed.

A method and an arrangement for measuring the soot particle content in the exhaust gases of an internal combustion engine are described in DE-A1-33 04 548. An insulator in the form of a ceramic plate is located in the exhaust pipe of the internal combustion engine. Two electrodes are arranged on the insulator at a distance from one another so that a gap is formed between the electrodes. When soot is formed in the exhaust gases, the soot adheres to the ceramic plate between the insulators. The soot then acts as an electric conductor between the electrodes. The quantity of soot on the ceramic plate is proportional to the resistance between the electrodes. The more soot that adheres to the ceramic plate, the smaller the resistance becomes. The resistance can then be measured and an idea of the soot particle content can thus be obtained.

In the case of a GDI engine and a diesel engine which, under certain operating conditions, work with a stratified air/fuel mixture, however, a measurement of the soot particle content in the exhaust pipe does not give an accurate picture of how complete the combustion of the fuel in the combustion chamber is.

SUMMARY OF THE INVENTION

One object of the present invention is to provide a method of the type indicated in the introduction which gives a picture of the particle content in the exhaust gases in the combustion chamber of an internal combustion engine.

A further object of the present invention is to provide a method of continuously measuring during operation of the engine the particle content in the exhaust gases in the combustion chamber of an internal combustion engine and, against the background of measurement values obtained, regulating the internal combustion engine so that a lower particle content in the exhaust gases is. obtained.

According to the invention, this is achieved by virtue of the fact that the sensor detects in at least one combustion chamber of the internal combustion engine a quantity, the size of which is dependent on the particle content in the exhaust gases, and that the level of a measurement signal output from the sensor, which signal is dependent on the detected quantity, is determined and compared with a desired value level of a signal which corresponds to a desired particle content in the exhaust gases.

Such a method of measuring the particle content in the exhaust gases provides a true picture of how complete the combustion of the fuel in the combustion chamber is. With a sensor located in the combustion chamber, such as the spark plug of a GDI engine and the heater plug of a diesel engine, simple and economical measuring equipment is obtained for measuring the particle content in the exhaust gases in the combustion chamber in conventional GDI and diesel engines.

BRIEF DESCRIPTION OF THE DRAWINGS

The invention will be described in greater detail below with reference to exemplary embodiments shown in the appended drawings, in which.

DETAILED DESCRIPTION OF THE PREFERRED EMBODIMENTS

Figure 1:
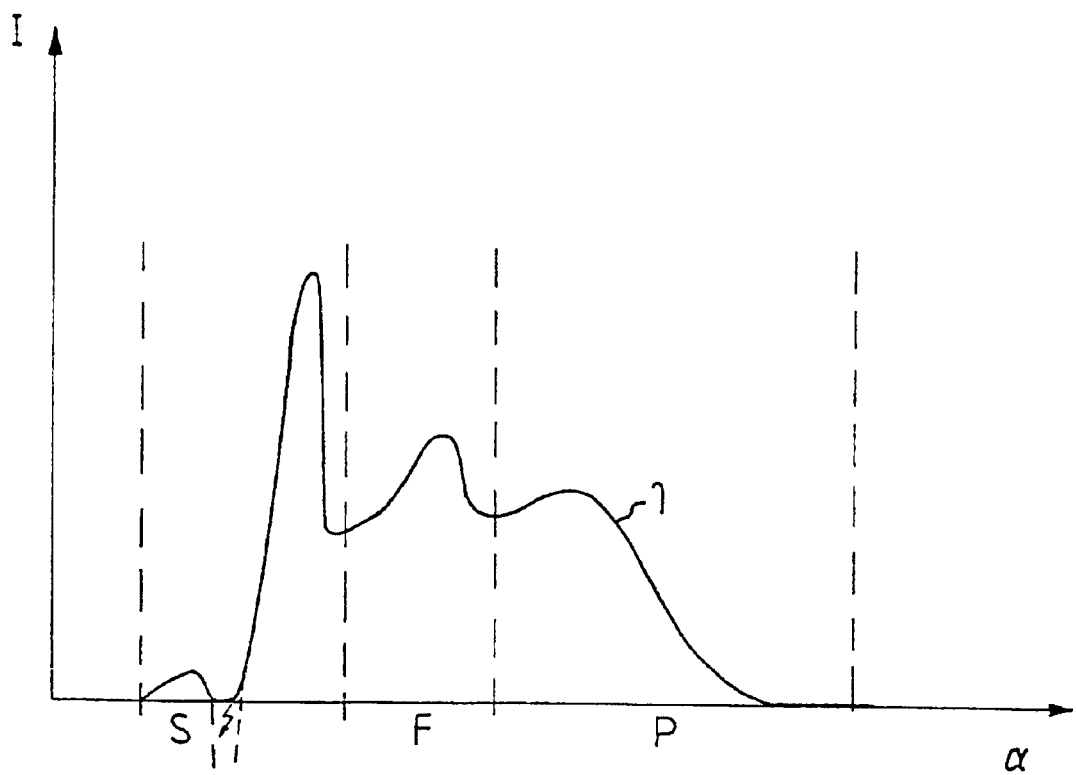
FIG. 1 relates to a coordinate system which shows the ionic current as a function of the crankshaft angle in the case of low soot particle content in the exhaust gases in the combustion chamber, FIG. 2 relates to a coordinate system which shows the ionic current as a function of the crankshaft angle in the case of a soot particle content in the exhaust gases in the combustion chamber which is greater than the soot particle content represented by the function in FIG. 1, FIG. 3 relates to a diagrammatically represented sensor and measuring unit in the case of a GDI engine, FIG. 4 relates to a diagrammatically represented sensor and measuring unit in the case of a diesel engine.
Figure 2:
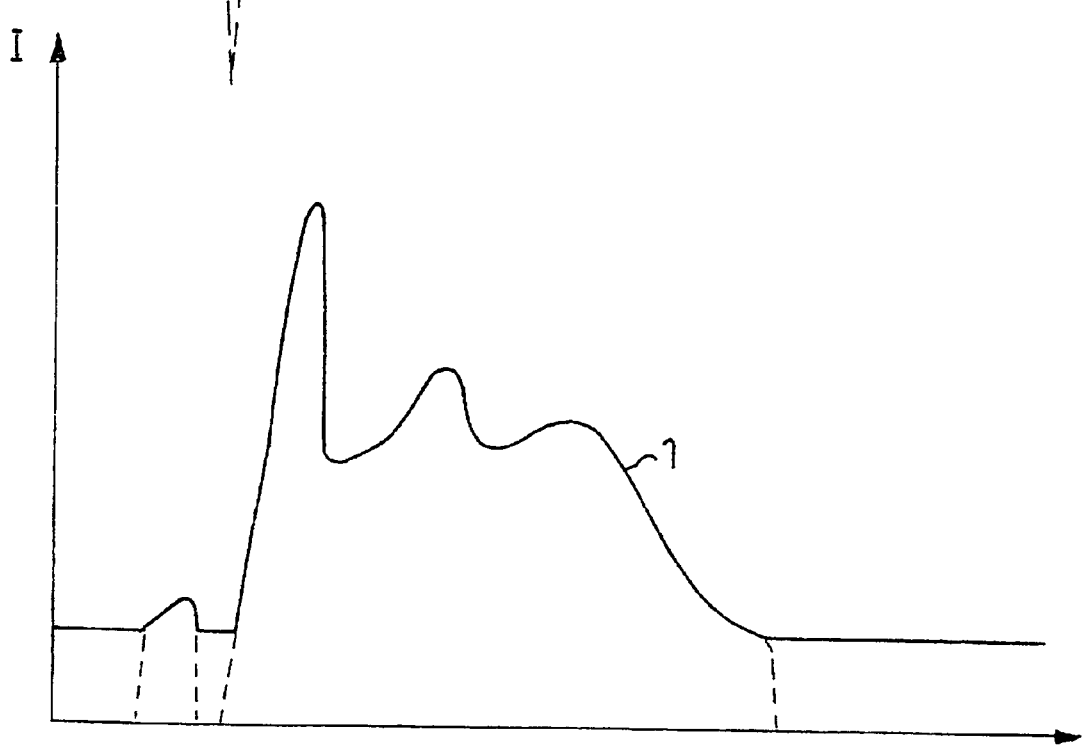

FIGS. 1 and 2 show a graph 1 which represents the ionic current $I_J$ that is formed in combustion chamber of a piston engine in connection with the combustion stoke. The graph 1 is drawn in a coordinate system where the X axis represents the crankshaft angle $\alpha$ and the Y axis represents the ionic current $I_J$. By arranging a sensor, which is connected to a measuring unit, in the combustion chamber, the ionic current signal shown in FIGS. 1 and 2 can be sampled in the measuring unit.

Figure 3:
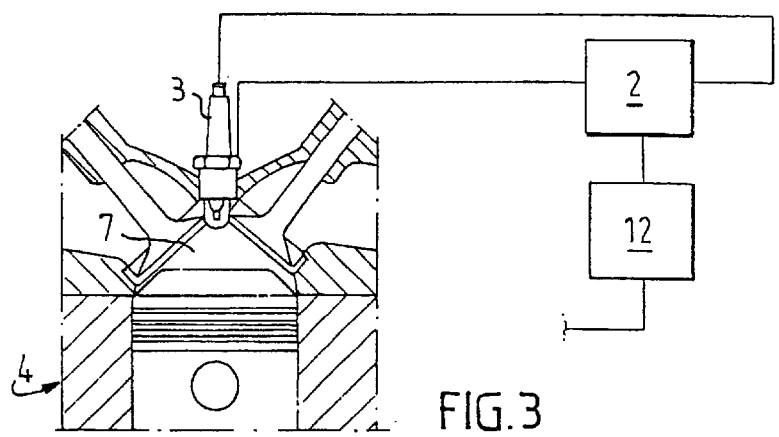

FIG. 3 shows an embodiment in which a measuring unit 2 is connected to the spark plug 3 of a GDI engine 4. The spark plug 3 therefore constitutes a sensor for providing signals to the measuring unit 2.

Figure 4:
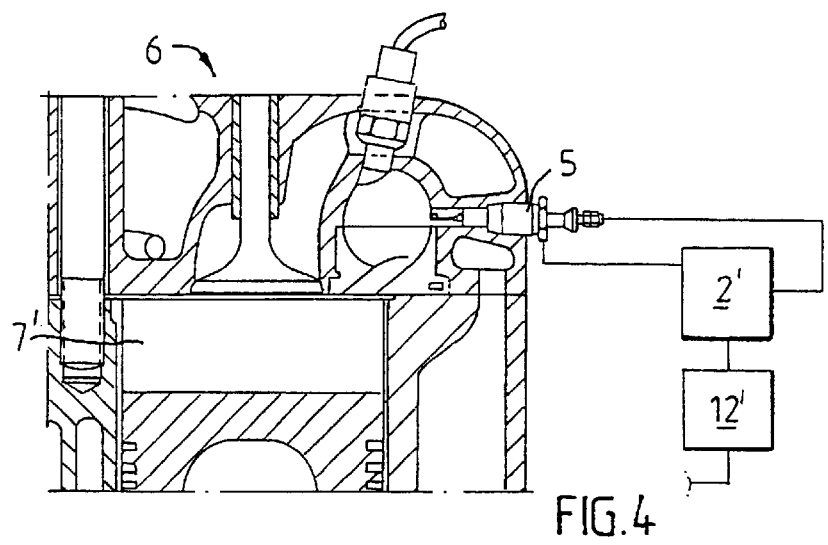

FIG. 4 shows another embodiment, in which a measuring unit 2' is connected to a heater plug 5 of a diesel engine 6 of the prechamber type. The heater plug 5 in this case constitutes a sensor which provides signals to the measuring unit 2'.

The graph for the ionic current signals shown in FIG. 1 consists of three different stages, namely the ignition stage S, the flame ionization stage F and the post-ionization stage P. During the ignition stage S, the charging action of the current in the ignition coil produces an interference which gives rise to a small current peak. A spark from the spark plug 3 then produces a strong pulse with a negative sign (broken line in FIG. 1). This negative pulse is filtered out. A large pulse then follows, which arises when the current to the spark plug 3 is broken. During the flame ionization stage F, a burning core of fuel/air mixture in or at the spark plug gap produces a pulse peak. During the post-ionization stage P, the combustion pressure in the combustion chamber 7 rises to its highest value and the flame front has then reached the walls of the combustion chamber 7.

According to the invention, a number of graphs for different operating conditions and different air/fuel, mixtures of an "ideal" internal combustion engine can be stored, in respect of which operating conditions and air/fuel mixtures a desired soot particle content in the exhaust gases is obtained. The level of these graphs is calculated and desired values are obtained for different operating conditions and air/fuel mixtures.

The level of the graph 1 means the position of the entire graph 1 above the X axis in the coordinate system. If the ionic current $I_J$ increases for each crankshaft angle α during the combustion stroke, the entire graph 1 is shifted upwards in the coordinate system, that is to say the level increases.

The level of the graph 1, which represents the ionic current $I_J$ that is detected by the sensor 3, 5 arranged in the combustion chamber 7, can be calculated in different ways in the measuring unit 2, 2' connected to the sensor. For example, one or more points of the sampled measurement signal, where the first derivative changes the sign from positive to negative, can be detected. Consequently, a value of the ionic current $I_J$ at the peaks of each stage S, F and P is then obtained. These values provide a measure of the level of the graph 1. Another way of obtaining the level of the graph 1 is to integrate the ionic current $I_J$ as a function of the time during the combustion stroke or a part thereof. The integral consequently provides the area under the graph 1, which is a measure of the level of the graph 1.

If the soot particle content in the exhaust gases increases, the level of the graph 1 above the X axis will increase, as shown in FIG. 2. The more the soot particle content increases, the higher the level of the graph 1 becomes.

This will be explained in greater detail below.

Figure 5:
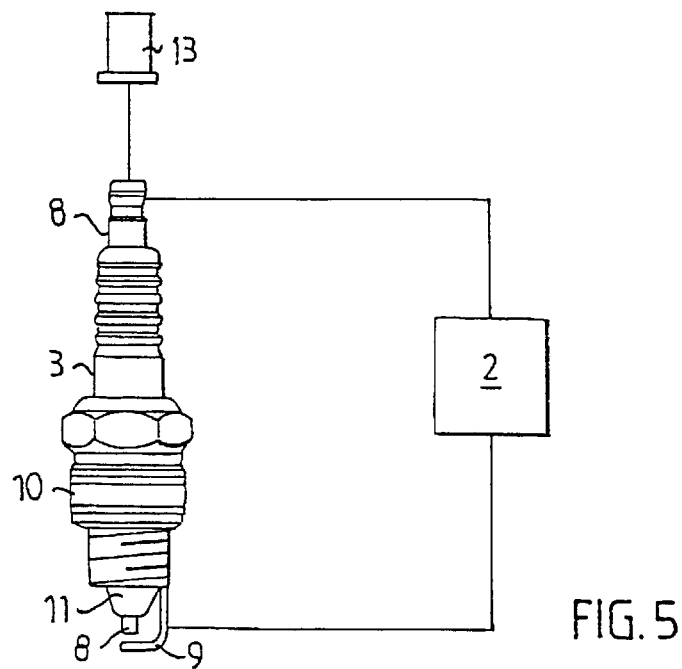
FIG. 5 shows a diagrammatic view of a measuring unit connected to a spark plug.

FIG. 5 shows a measuring unit 2 connected to a conventional spark plug 3. The measuring unit 2 is connected between the positive and negative (earth potential) electrodes 8 and 9 respectively of the spark plug 3. Between the positive electrode 8 and the housing 10 of the spark plug 3, in which housing the negative electrode 9 is arranged, there is an insulator 11 made of an electrically insulating material. FIG. 5 also shows diagrammatically how an ignition coil 13 is connected to the spark plug 3.

When soot particles are formed during the combustion stroke, these adhere to the insulator 11. The more soot particles that are formed, the thicker the soot deposit on the insulator 11 becomes. The soot particles conduct current, as a result of which a leakage current $I_L$ arises between the positive electrode 8 and the housing 10 which is connected to earth. The size of the leakage current $I_L$ is a measure of the soot particle content in the exhaust gases.

The leakage current affects the measurement of the ionic current $I_J$ in such a manner that when soot particles adhere to the insulator 11, the leakage current $I_L$ increases and thus the level of the ionic current signal also increases during measurement of the ionic current $I_J$. The more soot that adheres to the insulator 11, the more the level of the graph 1 representing the ionic current $I_J$ is raised.

The leakage current $I_L$ can itself be measured by a predetermined current being induced between the electrode 8 and the housing 10. The current that will then be transmitted between the electrode 8 and the housing 10 constitutes the leakage current $I_L$. FIG. 2 shows this leakage current $I_L$ as a straight line at the end of and after the post-ionization stage P and also before and during the ignition stage S. The leakage current $I_L$ is suitably measured at given defined crankshaft angles α or points in time, that is to say in given measurement windows, in which measurement windows the predetermined current is induced between the electrode 8 and the housing 10. The predetermined current that is induced between the electrode 8 and the housing 10 can be induced continuously during the cycle of the whole engine, that is to say during all strokes, for which a suitable measurement window can be defined by detecting the leakage current $I_L$ when the first derivative of the latter is zero for a continuous time interval.

Instead of measuring the leakage current $I_L$, it is possible to measure the impedance Z between the electrode 8 and the housing 10. As the soot particles that adhere to the insulator 11 conduct current, the impedance Z between the electrode 8 and the housing 10 will decrease when soot particles adhere to the insulator 11. When the impedance Z between the electrode 8 and the housing 10 is measured, the resistance, inductance and capacitance between the electrode 8 and the housing 10 will be taken into consideration at one and the same time of measurement. Instead of measuring the impedance Z, the resistance, inductance and capacitance can be measured individually.

A suitable measurement window for measuring the soot particle content in the combustion chamber 7, 7' may be during charging of the ignition coil 13 during the ignition stage F. This can be advantageous when the soot particle content is to be measured in a number of combustion chambers 7, 7' of the internal combustion engine 4, 6 because it then becomes simple to coordinate the measurements between the various sensors 3, 5.

By connecting the measuring unit 2 to the control unit 12 (see FIG. 3) of the internal combustion engine 4, the moment of ignition, the moment of fuel injection and/or the air/fuel mixture can be regulated so that the soot particle content in the exhaust gases decreases. When the soot particle content in the exhaust gases has decreased, the soot deposited on the insulator 11 will be burnt off during the combustion stroke.

Measurement of the soot particle content in a diesel engine 6 takes place in a similar manner to that described above. The heater plug 5 has an insulator (not shown), to which soot particles can adhere. The diesel engine 6 is also regulated by the measuring unit 2' being connected to a control unit 12' which adjusts the moment of fuel injection and the volume of fuel injected.

Instead of using the spark plug 3 or the heater plug 5 as the sensor, it is also possible for a separate sensor to be arranged in the combustion chamber 7, 7', which sensor has an insulator to which soot particles can adhere.

What is claimed is:

1. A method of measuring the soot particle content in combustion chamber gases of an internal combustion engine, comprising the steps of:

arranging a sensor in at least one combustion chamber of the internal combustion engine, in contact with the combustion chamber gases, the sensor comprising an insulator on which soot particles from the combustion chamber gases adhere;

using the sensor to detect, in the at least one combustion chamber, an electrical quantity, the size of which is dependent on the soot particle content in the combustion chamber gases;

measuring a level of a signal output from the sensor, which signal is dependent on the detected electrical quantity;

comparing the measured signal with a known optimal value level of a signal which corresponds to a known optimal soot particle content in combustion chamber gases; and sending a value obtained upon comparison of the measured level of the signal output from the sensor and the known optimal value level to a control unit arranged for the internal combustion engine, the unit regulating the internal combustion engine so that the soot particle content in the combustion chamber gases decreases, when the soot particle content is higher than the optimal value level.

2. The method according to claim 1, wherein the electrical quantity consists of a leakage current ($I_L$) which is transmitted between the sensor and earth potential and is formed by a predetermined current being induced between an electrode arranged on the sensor and the earth potential.

3. The method according to claim 1, wherein the electrical quantity consists of an impedance (Z) between an electrode arranged on the sensor and earth potential.

4. The method according to claim 2, wherein the electrical quantity ($I_L$, Z) is detected over a continuous time interval during which a first derivative is zero.

5. The method according to claim 2, wherein the electrical quantity ($I_L$, Z) is detected over a time during which an ignition coil arranged on the internal combustion engine is charged.

6. The method according to claim 1, wherein the electrical quantity consists of an ionic current ($I_I$) in the combustion chamber formed during combustion.

7. The method according to claim 6, wherein the measured signal output from the sensor is sampled for each crankshaft angle α during a combustion stroke of the internal combustion engine.

8. The method according to claim 6, wherein the level of the measured signal is calculated by detecting at least one point of the measured signal, where a first derivative changes the sign from positive to negative, the at least one point is compared with corresponding points of a signal which corresponds to the known optimal soot particle content in the combustion chamber gases.

9. The method according to claim 6, wherein the level of the measured signal is calculated by a function of the measured signal being integrated, which integral is compared with an integral of a function of a signal which corresponds to a known optimal soot particle content in the combustion chamber gases.

10. The method according to claim 1, wherein the method is applied to a piston engine with fuel injection directly into the combustion chamber, in which a spark plug constitutes the sensor.

11. The method according to claim 1, wherein the method is applied to a diesel engine in which a heater plug arranged in association with the combustion chamber constitutes the sensor.

12. The method according to claim 3, wherein the electrical quantity ($I_L$, Z) is detected over a continuous time interval during which a first derivative is zero.

13. The method according to claim 3, wherein the electrical quantity ($I_L$, Z) is detected over a time during which an ignition coil arranged on the internal combustion engine is charged.

14. A method of measuring the soot particle count of an internal combustion engine, comprising the steps of:

providing a sensor in a combustion chamber of the engine, the sensor including an insulator;

exposing the insulator to combustion in the combustion chamber so that soot particles adhere to the insulator;

measuring an electrical characteristic of the soot particles;

comparing the measured electrical characteristic with a known optimal electrical characteristic;

adjusting an air/fuel mixture provided to the combustion chamber based on the measured electrical characteristic.

15. A method of measuring the soot particle count of an internal combustion engine, comprising the steps of:

providing a sensor in a combustion chamber of the engine, the sensor including an insulator on which soot particles adhere;

measuring a signal output from the sensor based on an amount of soot particles adhered to the insulator;

comparing the measured signal with a known optimal signal;

controlling an air/fuel mixture provided to the combustion chamber based on whether the measured signal is greater than or less than the optimal signal.

16. The method of claim 14, wherein the sensor comprises a spark plug.

17. The method of claim 15, wherein the sensor comprises a spark plug.

18. The method of claim 14, wherein the electrical characteristic is current flow through the soot.

19. The method of claim 15, wherein the electrical characteristic is current flow through the soot.

20. The method of claim 14, wherein the electrical characteristic is impedance of the soot.

* * * * *